United States Patent
Wu et al.

(10) Patent No.: US 7,807,212 B2
(45) Date of Patent: Oct. 5, 2010

(54) PLASMA METHOD FOR TIOX BIOMEDICAL MATERIAL ONTO POLYMER SHEET

(75) Inventors: Te-Hsing Wu, Taoyuan County (TW); Ko-Shao Chen, Taipei (TW); Chia-Chieh Chen, Taoyuan County (TW); Lie-Hang Shen, Taoyuan County (TW); Yi-Chun Yeh, Yunlin County (TW); Nini-Chen Tsai, Chiayi County (TW)

(73) Assignee: Atomic Energy Council-Institute of Nuclear Energy Research, Taoyuan (TW)

( * ) Notice: Subject to any disclaimer, the term of this patent is extended or adjusted under 35 U.S.C. 154(b) by 1014 days.

(21) Appl. No.: 11/586,724

(22) Filed: Oct. 26, 2006

(65) Prior Publication Data
US 2007/0286942 A1 Dec. 13, 2007

(30) Foreign Application Priority Data
Jun. 9, 2006 (TW) .............................. 95120474 A (51) Int. Cl.
*B05D 3/06* (2006.01)
*H05H 1/00* (2006.01)
*H05H 1/24* (2006.01)
(52) U.S. Cl. .................. 427/2.1; 427/535; 427/536; 427/537; 427/539; 427/576
(58) Field of Classification Search ......... 427/2.1–2.31, 427/596, 597, 532, 535–537, 539

See application file for complete search history.

(56) References Cited

U.S. PATENT DOCUMENTS 4,704,299 A * 11/1987 Wielonski et al. ........... 427/488
5,612,049 A * 3/1997 Li et al. ...................... 424/422

OTHER PUBLICATIONS

Ahn et al. Variation of Structural and Optical properties of sol-gel TiO2 thin films. Materials Letters. vol. 57, Issue 30. Dec. 2003. pp. 4660-4666.*
Ichinose et al. Ultrathin Composite films: An indispensable resource for nanotechnology. Focused on nanotechnology. No. 37 Jul. 2001 pp. 34-37.*
Yang et al. TiO2 thin-films on polymer substrates and their photocatalytic activity. Thin Solid Films 495 (2006) pp. 266-271.*
Jung et al. Study of improvement technology of Photocatalytic Activity on teh TiO2 Sol by plasma treatment after dip-coating processing. Surface Review and Letters. vol. 10 No. 4 (2003) pp. 635-640.*
Chu et al. Plasma surface modification. Materials Science and Engineering R 36 (2002) pp. 143-206.*
Hashizume et al. Preparation and functionalization of self-supporting (polymer/metal oxide) composite ultrathin films. Focused on Nanotechnology in Riken II. No. 38 (Aug. 2001) pp. 36-39.*

* cited by examiner

*Primary Examiner*—Timothy H Meeks
*Assistant Examiner*—Cachet I Sellman
(74) *Attorney, Agent, or Firm*—Jackson IPG PLLC; Demian K. Jackson (57) ABSTRACT

A biomedical material is prepared through a plasma method. The material is a film containing titanium oxide onto polymer sheet. The film is hydrophilic, bacterial inactivated and biocompatible. The present invention can be applied to artificial guiding tube and wound dressing material.

17 Claims, 15 Drawing Sheets

| Pseudomonas aeruginosa broth | Origin | 30s | 3min | 5min | 10min | 15min | 30min | 45min | 60min |
|---|---|---|---|---|---|---|---|---|---|
| $10^6$ | N | 243 | 370 | 228 | 417 | 211 | 426 | 54 | 521 |
| $10^7$ | 181 | 35 | 52 | 13 | 61 | 45 | 50 | 8 | 66 |
| $10^8$ | 30 | 2 | 2 | 2 | 2 | 2 | 6 | 0 | 11 |

FIG.4D

PLASMA METHOD FOR TIOX BIOMEDICAL MATERIAL ONTO POLYMER SHEET

FIELD OF THE INVENTION

The present invention relates to a plasma method; more particularly, relates to preparing a biomedical material having hydrophile, photo-induced inactivation and bio-compatibility.

DESCRIPTION OF THE RELATED ART

Environment protection and health caring are two of the major concerns to human's life today. Green productions and health caring medicines therefore become more and more popular. Titanium dioxide ($TiO_x$) is a semiconductor having great abilities in oxidation and reduction and is made into a photo catalysis widely used for defogging, deodorizing and sterilizing. Regarding the fabric base for $TiO_x$, porous polymer is used. For example, stretchable Teflon, like expanded PTFE (ePTFE), is porous, safe and biocompatible and is suitable to be applied in a nano-grade processed material. But, stretchable Teflon is a bioinert material and is a non-decomposable material having a water repellent surface. Thus, a surface modification is required for such a material to function well.

There are a few methods for the surface modification. One which uses low-temperature plasma does not destroy surface structure and can be operated under a normal environment with low pollution. A prior art for preparing a temporary wound dressing by surface grafting polymerization with gamma-ray irradiation is revealed. The prior art uses a plasma or a gamma-ray irradiation on a material surface for grafting with a hydrophilic monomer, like acrylamide or itaconic acid, to improve hydrophile for hydrophilic decomposable polymer. Then a nonwoven wound dressing is made easy-stripped. Finally, a biodegradable material, like gelatin, chondroitin-6-sulfate or chitosan, is fixed on the surface of the dressing with special functional group, like —$NH_2$, polymerized on a grafting layer. By doing so, a biocompatibility is gained to help histiocyte on regenerating and repairing. On considering that wound is apt to be infected by germs in the air, an anti-bacterial agent is further applied to prevent unwanted result to the wound owing to infection. The dressing is processed through a gamma-ray irradiation or a plasma activation treatment and is processed with a surface grating polymerization using a monomer, like a thermo-sensitive monomer of N-isopropylacrylamide (NIPAAm), a water-soluble monomer of acrylamide (AAm) or an itaconic acid. Or, the dressing is directly processed through a grating polymerization with gamma-ray for surface grating. Hence, an immobilization with chemical cross linking is used to fix different biodegradable protein to obtain biodegradability and regeneration ability. In the other hand, different fixing methods are applied to different contact area of air, coordinated with different chemical structures of anti-bacterial agents.

Although the above prior art prepares an anti-bacterial and hydrophilic biomedical material, the procedure is complex and a few agent are required. Hence, the prior art does not full users' requests on actual use.

SUMMARY OF THE INVENTION

The main purpose of the present invention is to prepare a biomedical material having hydrophile, photo-induced inactivation and bio-compatibility through a surface modification with plasma to obtain a hydrophilic polymer film, where the procedure is simple and no additional agent of initiator or catalyst is required.

To achieve the above purpose, the present invention is a plasma method for a $TiO_x$ biomedical material onto polymer sheet, comprising steps of: (a) obtaining a hydrophilic polymer film to be coated with an organic titanium solution through a sol-gel method; and (b) processing a plasma activation treatment with oxygen having a pressure to the hydrophilic polymer film under a vacuum pressure to obtain a $TiO_x$ film onto polymer sheet, where the $TiO_x$ film onto polymer sheet obtained after step (b) is further processed through a copolymerization in surface grafting to enhance hydrophile and to increase sterilized are a on a surface of the polymer film. Accordingly, a novel plasma method for a $TiO_x$ biomedical material onto polymer sheet is obtained.

BRIEF DESCRIPTIONS OF THE DRAWINGS

The present invention will be better understood from the following detailed descriptions of the preferred embodiments according to the present invention, taken in conjunction with the accompanying drawings, in which.

DESCRIPTIONS OF THE PREFERRED EMBODIMENTS

The following descriptions of the preferred embodiments are provided to understand the features and the structures of the present invention.

Figure 1:
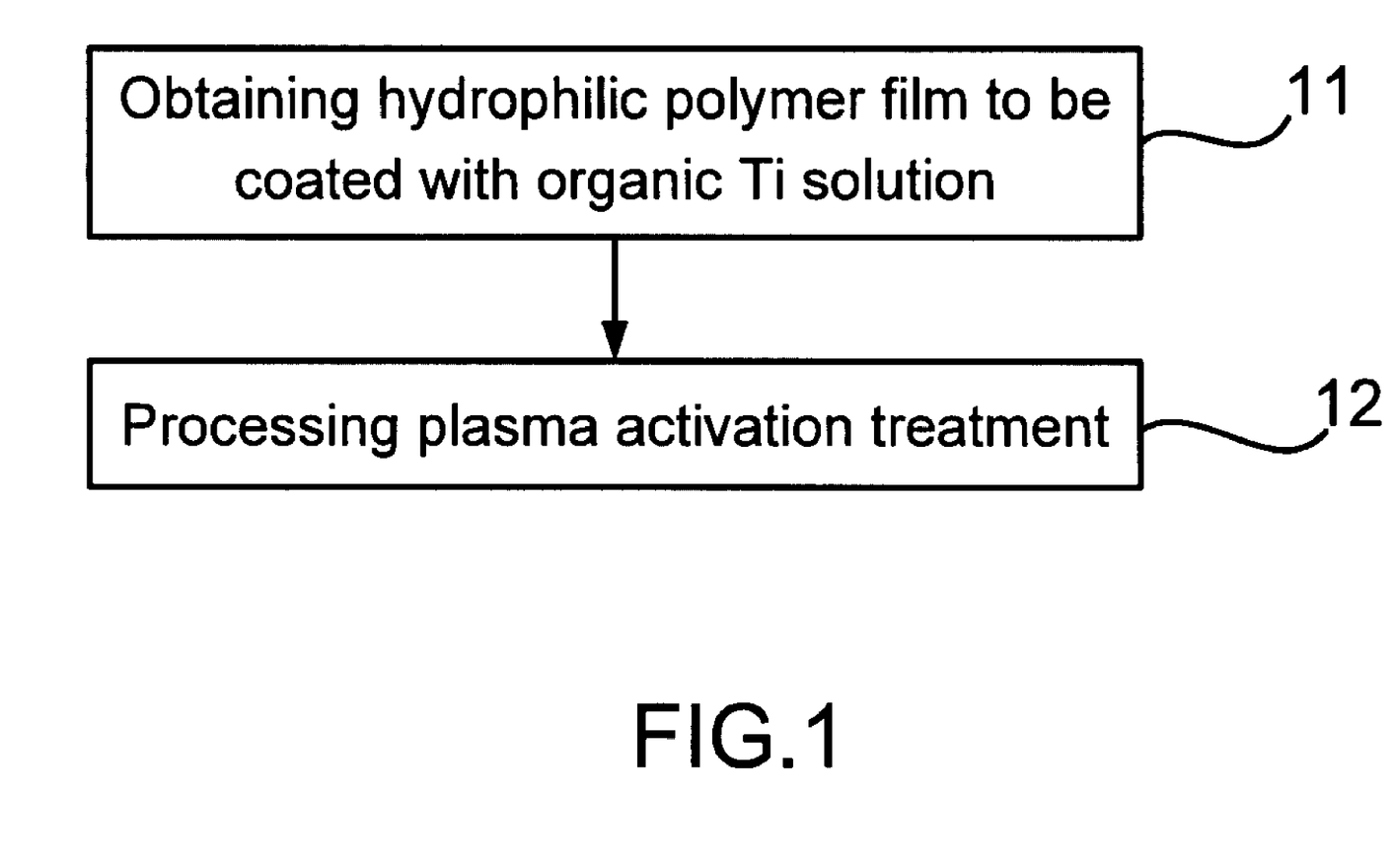
FIG. 1 is the view showing the flow chart according to the present invention.

Please refer to FIG. 1, which is a view showing a flow chart according to the present invention. As shown in the figure, the present invention is a plasma method for a titanium oxide ($TiO_x$) biomedical material onto polymer sheet, comprising the following steps:

(a) Obtaining a hydrophilic polymer film to be coated with an organic titanium (Ti) solution 11: A hydrophilic polymer film is coated with an organic Ti solution formed through a sol-gel method, where the hydrophilic polymer film is a polymer film made of hexamethyldisilazane (HMDSZ), itaconic acid or acrylamide; and the polymer film is a stretchable Teflon or a poly lactic-co-glycolic acid (PLGA). The sol-gel method comprises steps of: (i) dissolving a precursor of Ti Isopropoxide (TIP) into an organic solution; (ii) obtaining an organic Ti solution by using ultrasonic waves; and (iii) spin-coating the organic Ti solution on the hydrophilic polymer film.

(b) Processing a plasma activation treatment 12: certain pressure of oxygen ($O_2$) is accessed to the hydrophilic polymer film coated with the organic Ti solution for processing a plasma activation treatment under a certain vacuum pressure with an $O_2$ plasma to obtain a $TiO_x$ film onto polymer sheet. There in, the vacuum pressure is lower than 50 mtorr; the pressure for $O_2$ is between 150 and 250 mtorr; and the working power for the $O_2$ plasma is greater than 10 watts (W).

Thus, a $TiO_x$ biomedical material onto polymer sheet is obtained.

Figure 2:
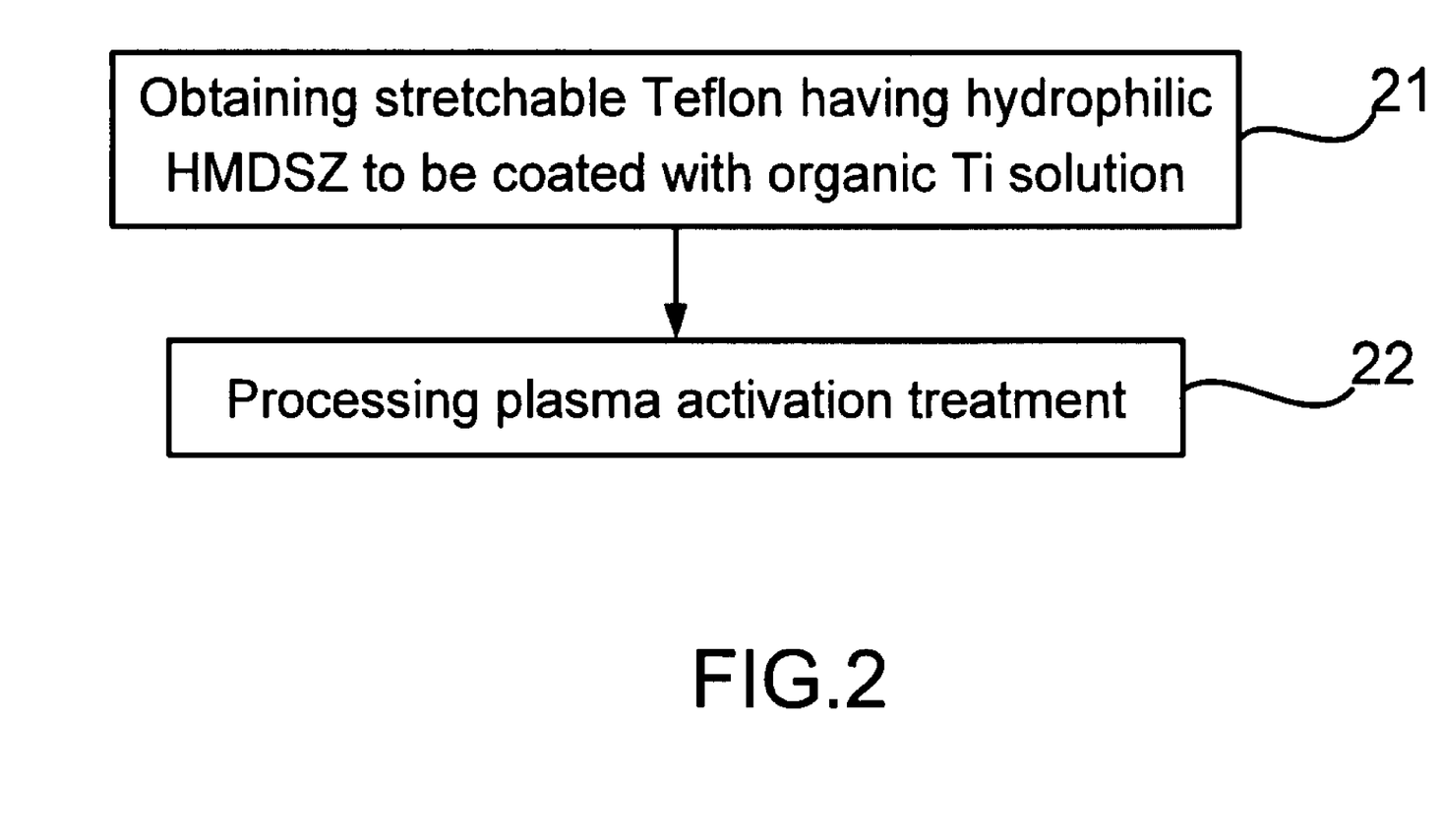
FIG. 2 is the view showing the flow chart of the first preferred embodiment.

Please refer to FIG. 2, which is a view showing a flow chart of a first preferred embodiment. As shown in the figure, a hydrophilic polymer film used in a first preferred embodiment is a stretchable Teflon having hydrophilic HMDSZ to obtain a $TiO_x$ biomedical material onto polymer sheet according to the present invention, comprising the following steps:

(a) Obtaining a stretchable Teflon having hydrophilic HMDSZ to be coated with an organic Ti solution 21: A stretchable Teflon having hydrophilic HMDSZ is coated with an organic Ti solution formed through a sol-gel method, where the sol-gel method comprises steps of: (i) dissolving a precursor of TIP into an organic solution; (ii) obtaining an organic Ti solution by using ultrasonic waves; and (iii) spin-coating the organic Ti solution on the stretchable Teflon having hydrophilic HMDSZ.

(b) Processing a plasma activation treatment 22: An $O_2$ having a pressure between 150 and 250 mtorr is accessed to the stretchable Teflon coated with the organic Ti solution for processing a plasma activation treatment under a 50 mtorr vacuum pressure, where the working power is greater than 10 W and the plasma activation treatment is processed for a time between 10 and 100 minutes (min). Thus, a $TiO_x$ film onto a stretchable Teflon is obtained.

Figure 2A:
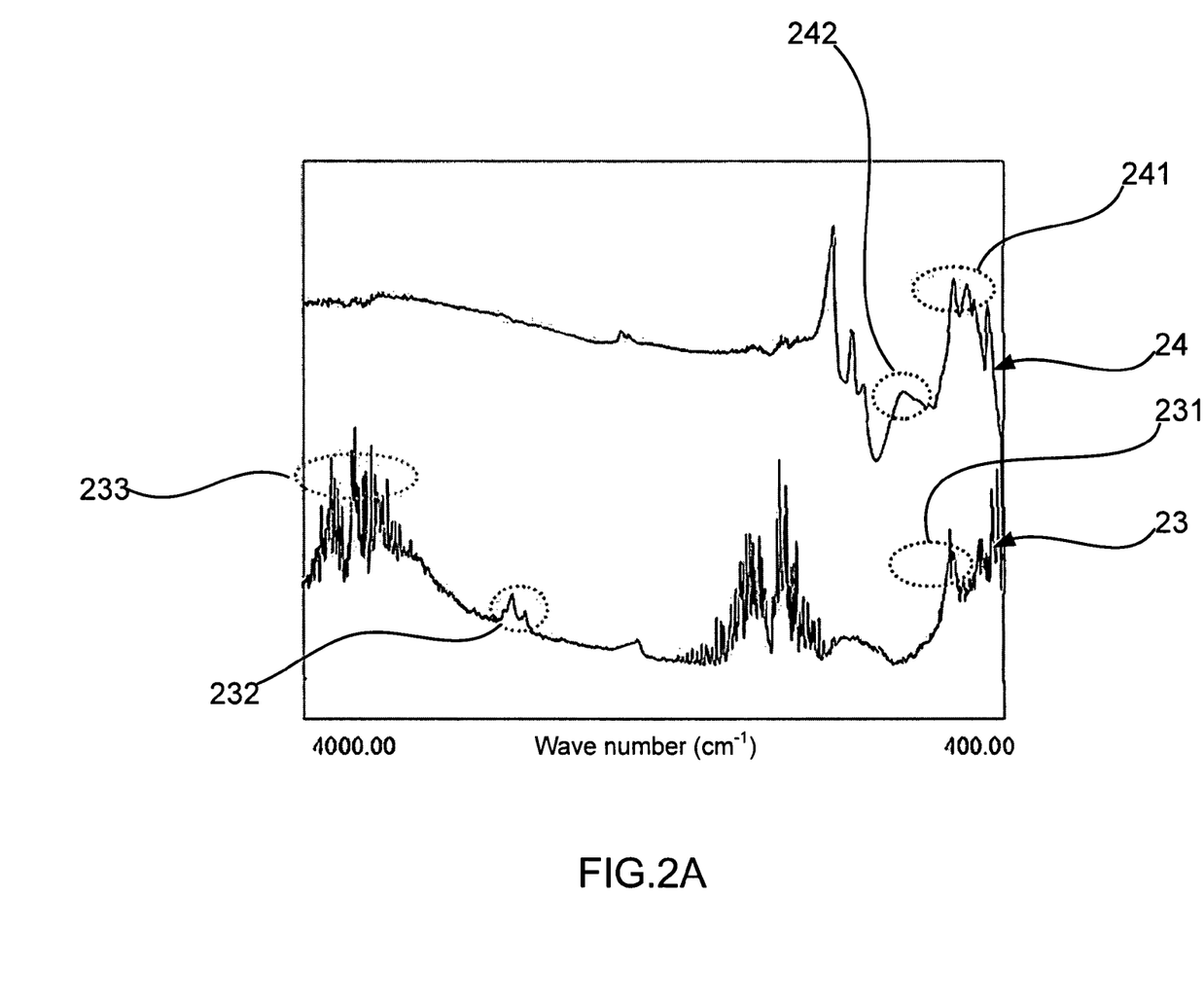
FIG. 2A is the view showing the Fourier transform infrared spectrum of the first preferred embodiment.

Please refer to FIG. 2A, which is a view showing a Fourier transform infrared spectrum of the first preferred embodiment. As shown in the figure, a Fourier transform infrared spectroscopy analysis is processed to a stretchable Teflon coated with an organic Ti solution, and a $TiO_x$ film onto polymer sheet after a plasma activation treatment, to obtain a first spectrum curve 23 and a second spectrum curve 24, respectively. A Ti—O characteristic absorption peak 231 is found at a wave number about 699 $cm^{-1}$ on the first spectrum curve 23; a C—H peak 232, at about 2952 $cm^{-1}$; and a O—H peak 233, at about 3600 $cm^{-1}$.

The second spectrum curve 24 shows a Ti—O characteristic absorption peak 241 like the first spectrum curve 23. After the plasma activation treatment, the organic material in the organic Ti solution is dissolved out from the stretchable Teflon coated with the organic Ti solution and is oxidized. The originally weak Ti—O characteristic absorption peak 231 is thus enhanced to obtain the Ti—O characteristic absorption peak 241 of the second spectrum curve 24 after the plasma activation treatment, where a C—O characteristic absorption peak 242 is also shown at a wave number between 900 and 1100 $cm^{-1}$. Thus, a Ti—O linking film is formed on a surface of a polymer film of stretchable Teflon to obtain a $TiO_x$ film on stretchable Teflon according to the present invention.

Figure 2B:
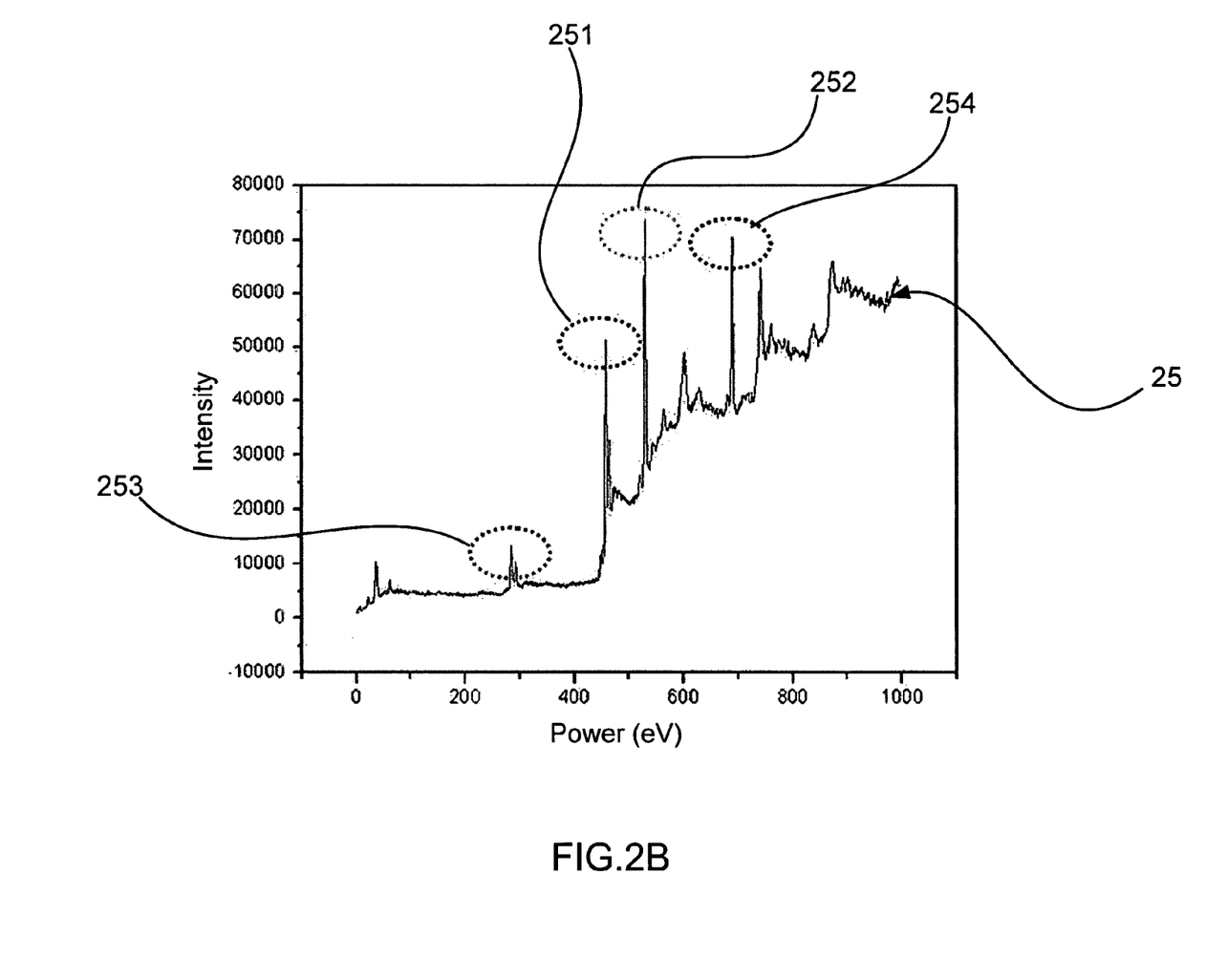
FIG. 2B to FIG. 2D are the views showing the distribution curves of the first, the second and the third elements of the first preferred embodiment.

Please refer to FIG. 2B, which is a view showing a distribution curve of a first element of the first preferred embodiment. As shown in the figure the $TiO_x$ film on the stretchable Teflon is processed through an electron spectroscopy for chemical analysis to obtain a distribution curve of a first chemical element 25.

In the distribution curve of the first chemical elements 25, a Ti peak 251 is shown at 458.8 eV and an O peak 252 is shown at 531.0 eV, together with a carbon (C) peak 253 and a fluorine (F) peak 254.

Figure 2C:
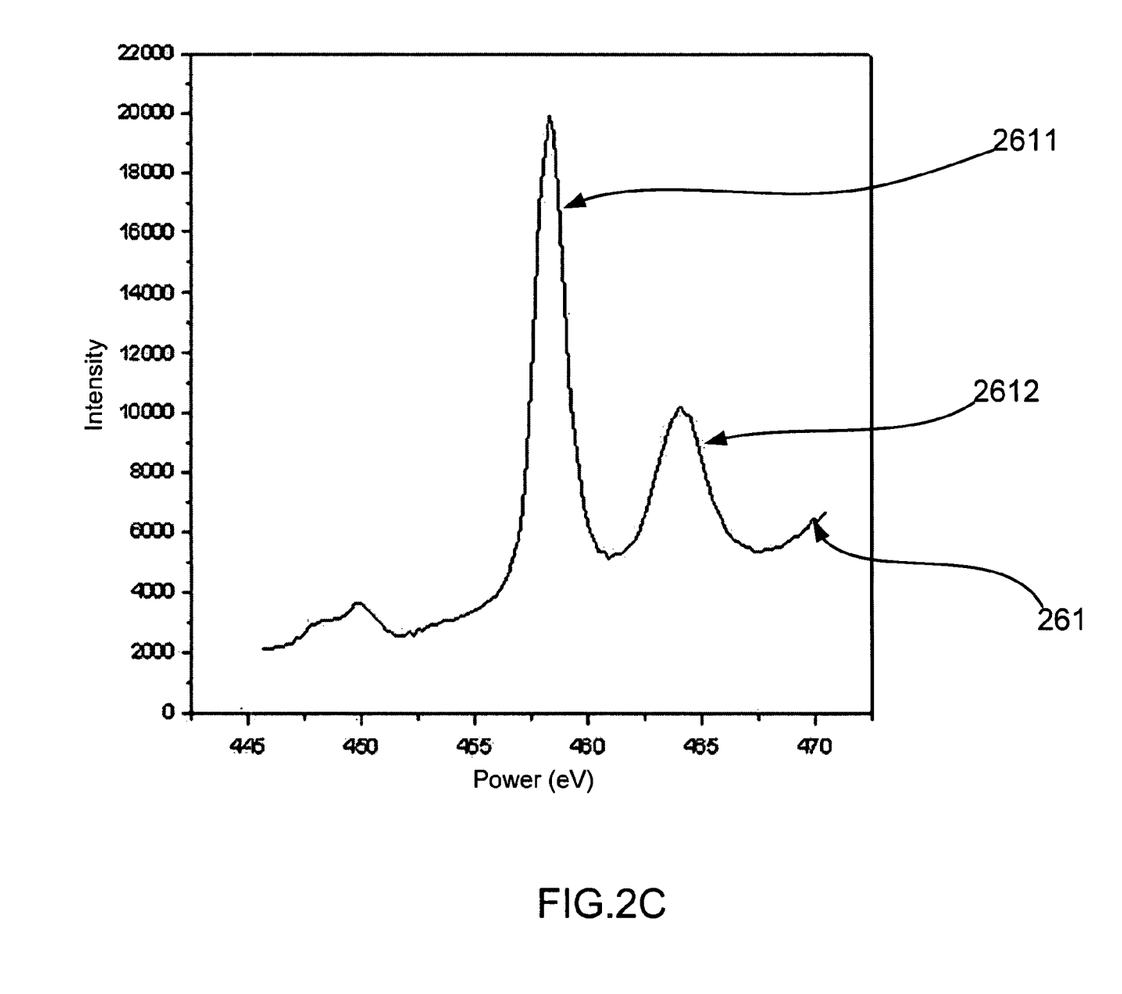
Figure 2D:
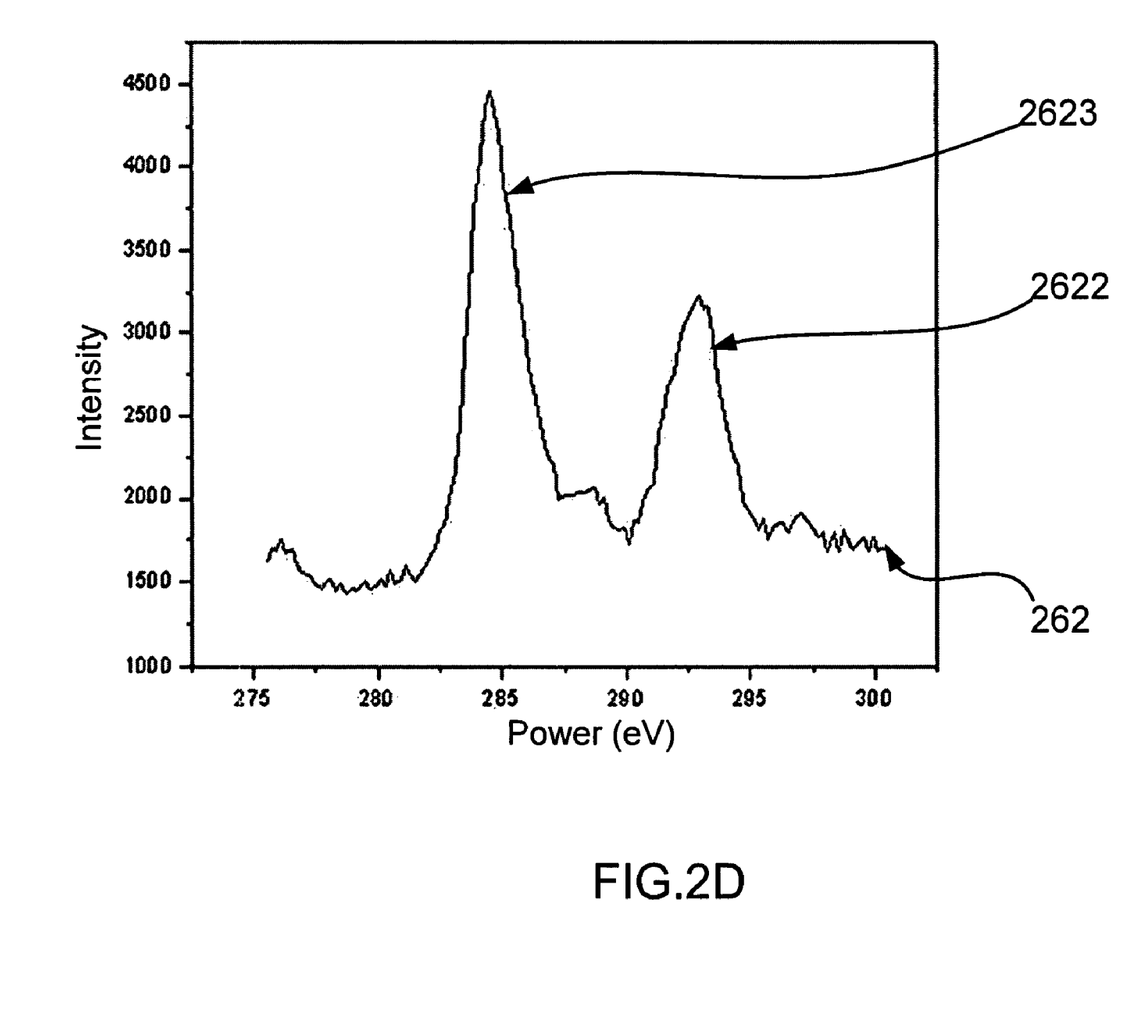

Please refer to FIG. 2C and FIG. 2D, which are views showing distribution curves of the second and the third elements of the first preferred embodiment. As shown in the figures, distribution curves of Ti element 261 and C element 262 in the $TiO_x$ film onto polymer sheet are displayed. In the distribution curve of the Ti element 261, a Ti 2p3/2 peak 2611 is shown at a power of 458.8 eV; and a Ti 2p1/2 peak 2612, at a power of 464 eV. In the distribution curve of the C element 262, a C peak 2621 is shown at a power of 284.5 eV; and a carbon fluoride ($CF_2$) peak 2622, at 292 eV.

Figure 3:
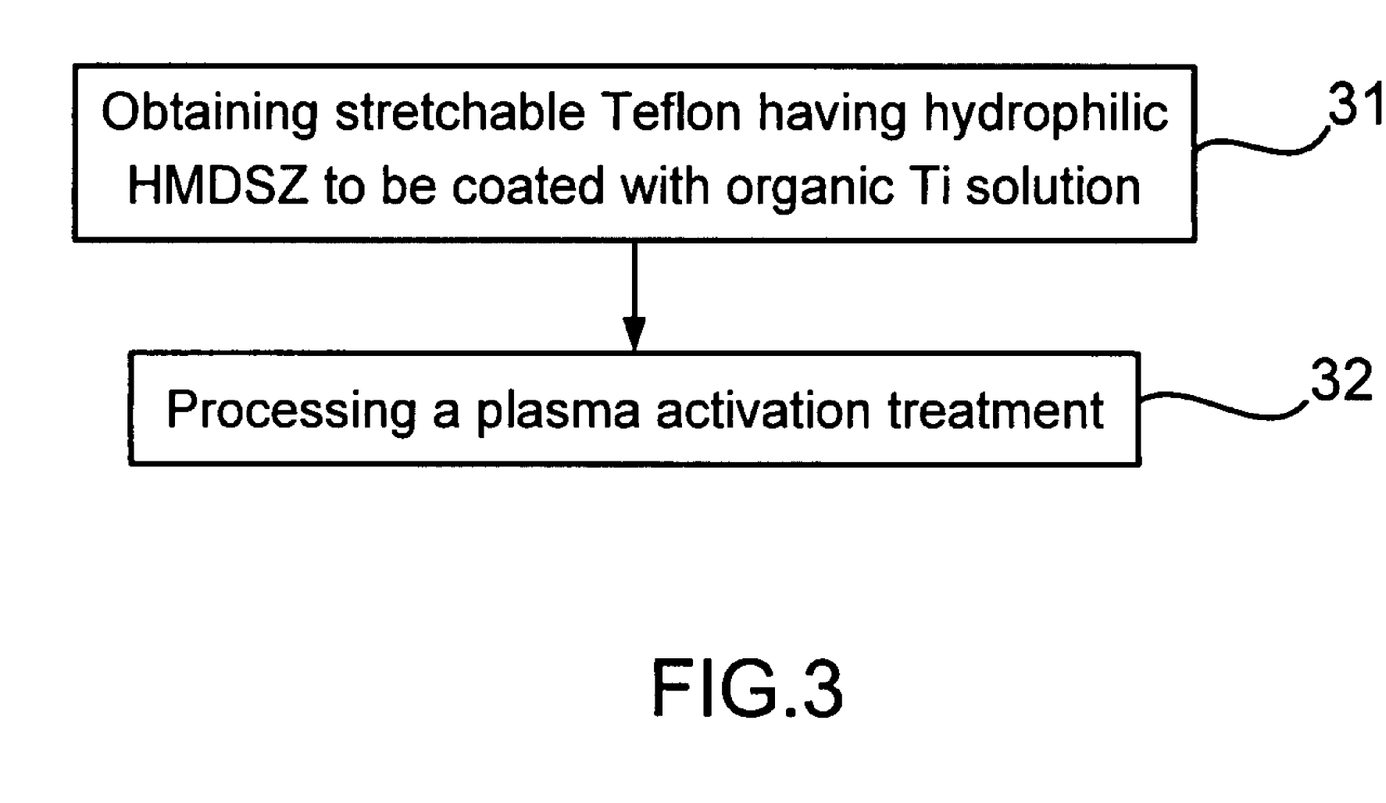
FIG. 3 is the view showing the flow chart of the second preferred embodiment.

Please refer to FIG. 3, which is a view showing a flowchart of a second preferred embodiment. As shown in the figure, a hydrophilic polymer film used in a second preferred embodiment is a stretchable Teflon having hydrophilic HMDSZ to obtain a $TiO_x$ biomedical material onto polymer sheet according to the present invention, comprising the following steps:

(a) Obtaining a stretchable Teflon having hydrophilic HMDSZ coated with an organic Ti solution 31: A stretchable Teflon having hydrophilic HMDSZ is coated with an organic Ti solution formed through a sol-gel method, where the sol-gel method comprises steps of: (i) dissolving a precursor of TIP into an organic solution; (ii) obtaining an organic Ti solution by using ultra sonic waves and (iii) spin-coating the organic Ti solution on the stretchable Teflon having hydrophilic HMDSZ.

(b) Processing a plasma activation treatment 32: An $O_2$ having a pressure between 150 and 250 mtorr is accessed to the stretchable Teflon coated with the organic Ti solution for processing a plasma activation treatment under a 50 mtorr vacuum pressure, where the working power is greater than 10 W and the plasma activation treatment is processed for 15 min. Thus, a $TiO_x$ film onto a stretchable Teflon is obtained.

Figure 3A:
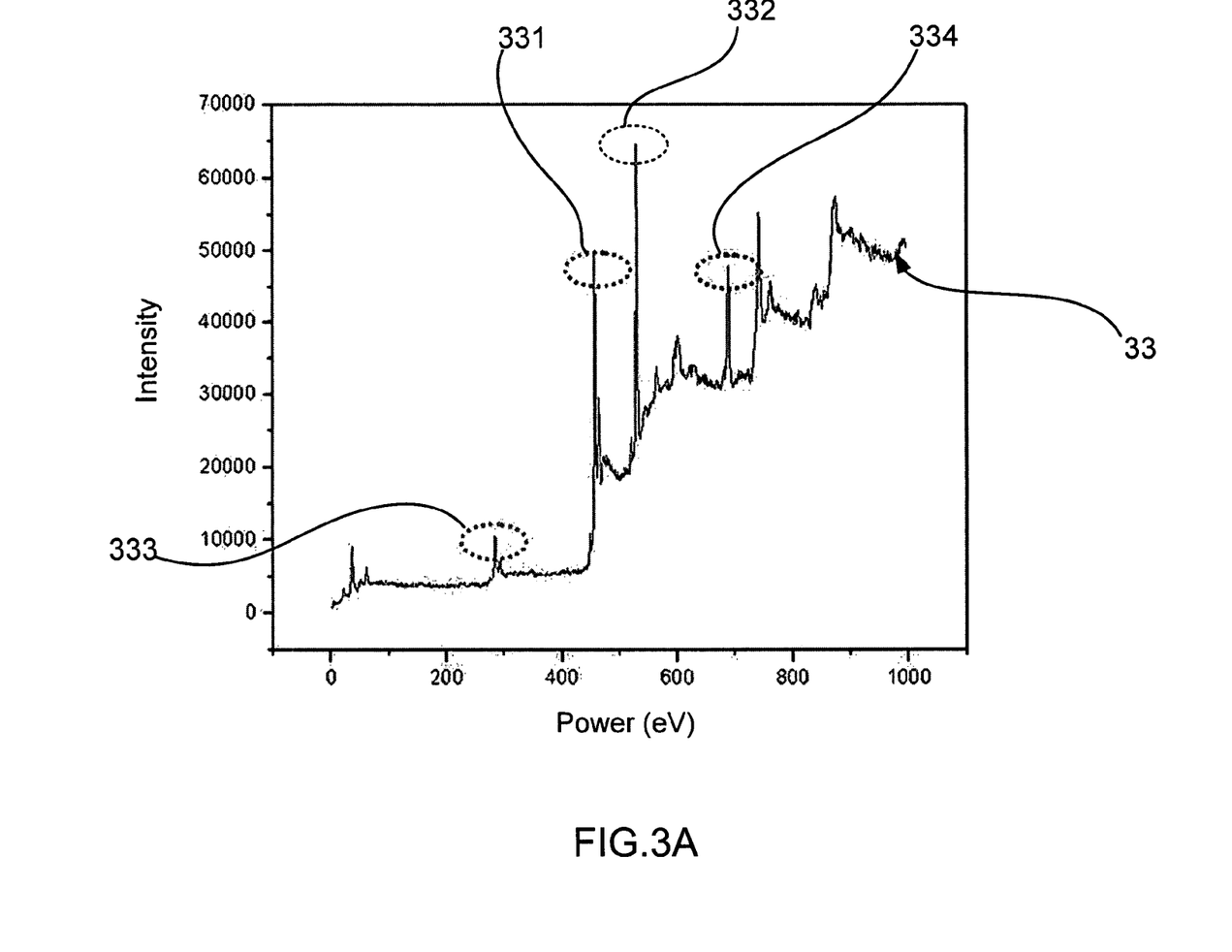
FIG. 3A to FIG. 3C are the views showing the distribution curves of the first, the second and the third elements of the second preferred embodiment.

Please refer to FIG. 3A, which is a view showing a distribution curves of a first element of the second preferred embodiment. As shown in the figure, a $TiO_x$ film onto polymer sheet is processed through an electron spectroscopy for chemical analysis to obtain a distribution curve of a second chemical element 33. A Ti—O peak 331 is found at a power about 458.8 eV; and an O peak 332, at about 531.0 eV; along with a C peak 333 and an F peak 334.

Figure 3B:
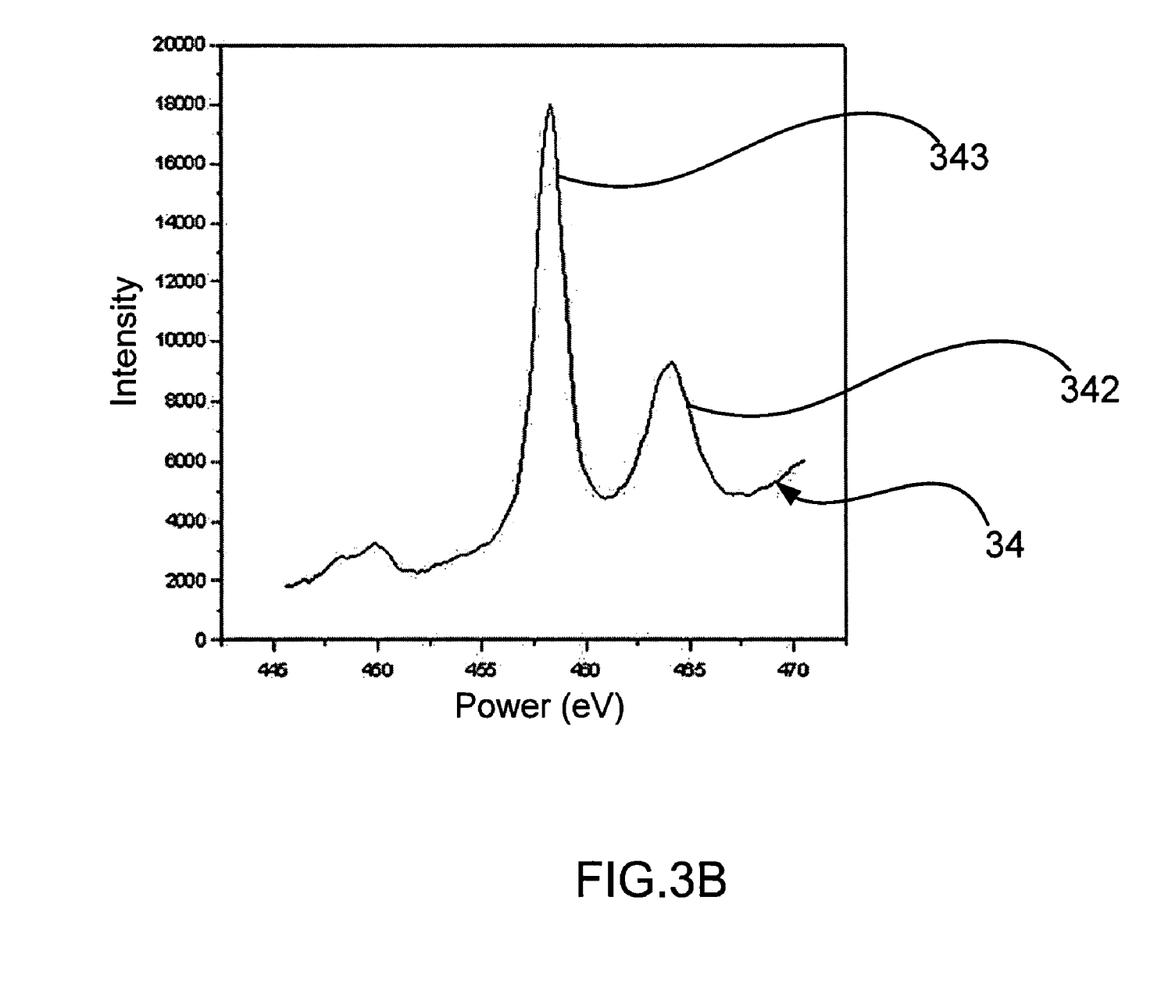
Figure 3C:
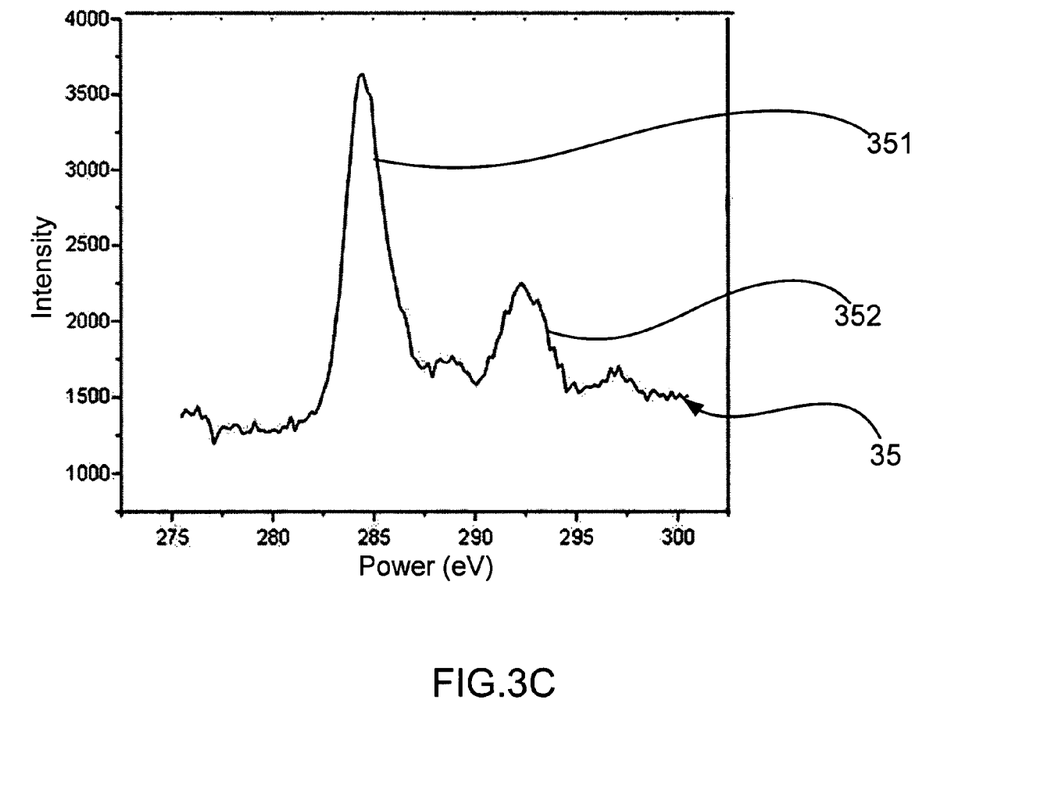

Please refer to FIG. 3B and FIG. 3C, which are views showing distribution curves of the second and the third elements of the second preferred embodiment. As shown in the figures, distribution curves of Ti element 34 and C element 35 in the $TiO_x$ film onto polymer sheet are displayed. In the distribution curve of the Ti element 34, a Ti 2p3/2 peak 341 is shown at a power of 458.8 eV; and a Ti 2p1/2 peak 342, at a power of 464 eV. In the distribution curve of the C element 35, a C peak 351 is shown at a power of 284.5 eV; and a $CF_2$ peak 352, at 292 eV.

In FIG. 3B and FIG. 3C, two highest intensities are found in the distribution curves for the Ti element 34 and the C element 35 separately. These two intensities are both smaller than those two highest intensities found in the distribution curves for the Ti element 261 and the C element 262 in FIG. 2C and FIG. 2D respectively. In the process of the plasma activation treatment, crystallization to the TiOR film happens on the surface of the polymer film owing to the heat generated. As time goes by on processing the plasma activation treatment, more crystallization happens to the TiOR film and the intensity becomes higher.

Figure 4:
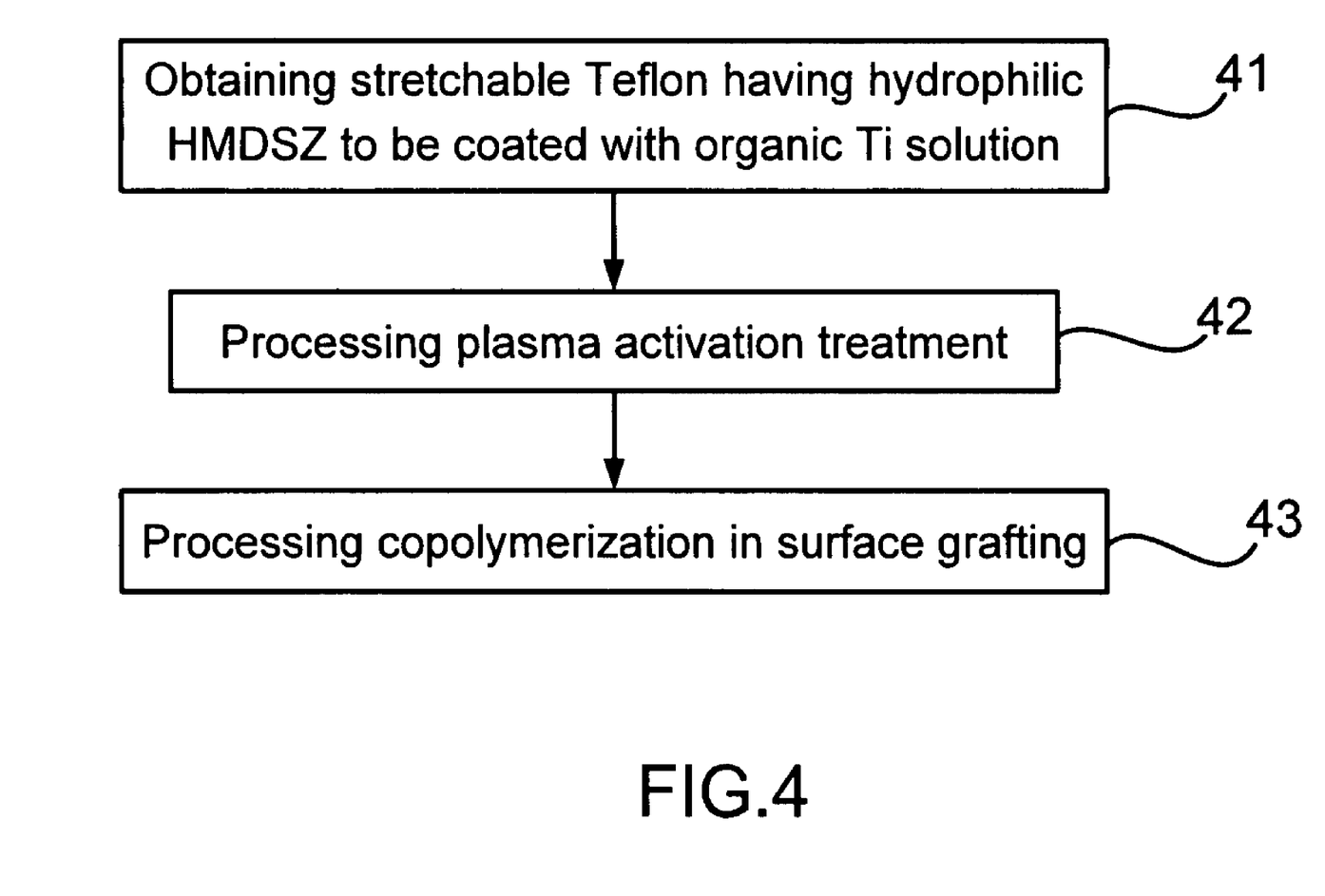
FIG. 4 is the view showing the flow chart of the third preferred embodiment.
Figure 4A:
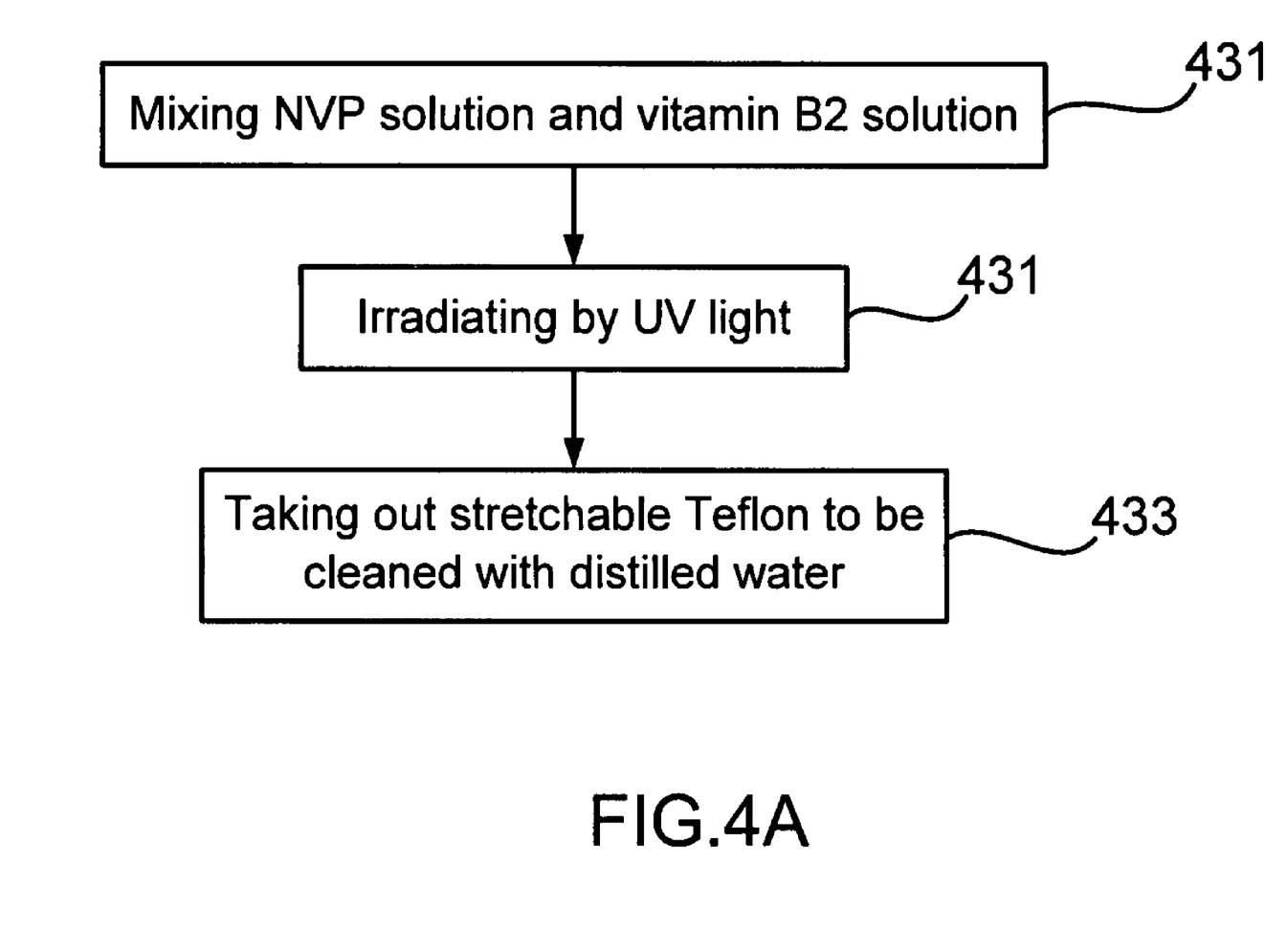
FIG. 4A is the view showing the flow chart of step (c)

Please refer to FIG. 4 and FIG. 4A, which are views showing flow charts of a third preferred embodiment itself and its step (c). As shown in the figures, the hydrophilic polymer film used in the present invention is a stretchable Teflon having hydrophilic HMDSZ and is made into a $TiO_x$ film on the stretch able Teflon through the following steps:

(a) Obtaining a stretchable Teflon having hydrophilic HMDSZ to be coated with an organic Ti solution 41: A stretchable Teflon having hydrophilic HMDSZ is obtained through a sol-gel method to be coated with an organic Ti solution, where the sol-gel method comprises steps of: (i) dissolving a precursor of TIP into an organic solution; (ii) obtaining an organic Ti solution by using ultra sonic waves; and (iii) sp in coating the organic Ti solution on the stretch able Teflon having hydrophilic HMDSZ.

(b) Processing a plasma activation treatment 42: An $O_2$ having a pressure between 150 and 250 mtorr is accessed to the stretchable Teflon coated with the organic Ti solution for processing a plasma activation treatment under a 50 mtorr vacuum pressure to obtain a $TiO_x$ film onto a stretchable Teflon, where the working power is greater than 10 W.

(c) Processing a copolymerization in surface grafting 43: The $TiO_x$ film onto a stretchable Teflon is processed with a copolymerization in surface grafting, comprising the following steps:

(c1) Mixing NVP solution and vitamin B2 solution 431: The $TiO_x$ film onto a stretchable Teflon is mixed into a solution of N-Vinyl-2-pyrrolidinone (NVP) less than 30 weight percents (wt %). The solution is then added with a certain amount of vitamin B2 solution in a rate of 4:1 while being accessed with nitrogen for 30 min.

(c2) Irradiating by UV light 432: The above mixed solution having the $TiO_x$ film onto a stretchable Teflon is irradiated by an ultra-violet light for 5 to 30 min.

(c3) Taking out stretchable Teflon to be cleaned with distilled water 433: The stretchable Teflon is taken out and is cleaned with a distilled water for less than 40 hours to remove homopolymer and unreacted monomer.

Figure 4B:
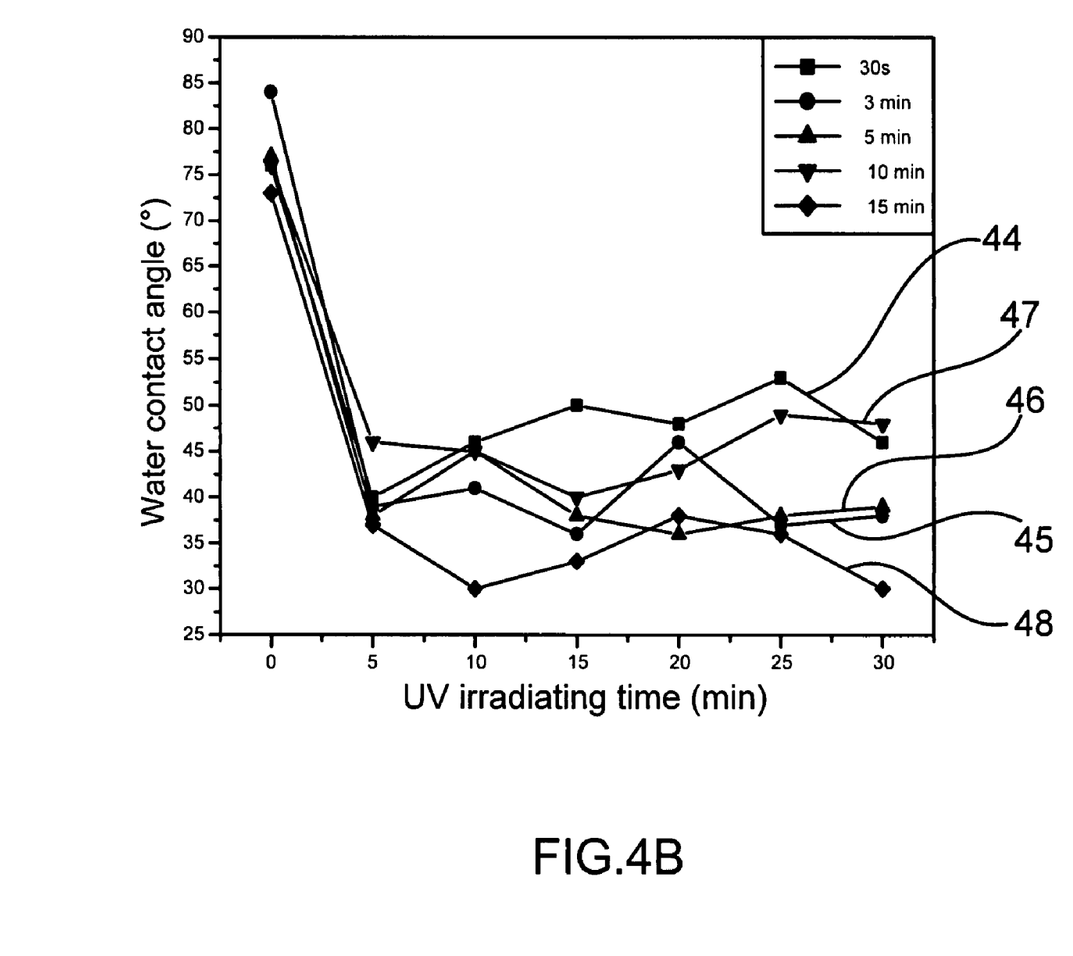
FIG. 4B and FIG. 4C are the first and the second views showing the water contact angle.
Figure 4C:
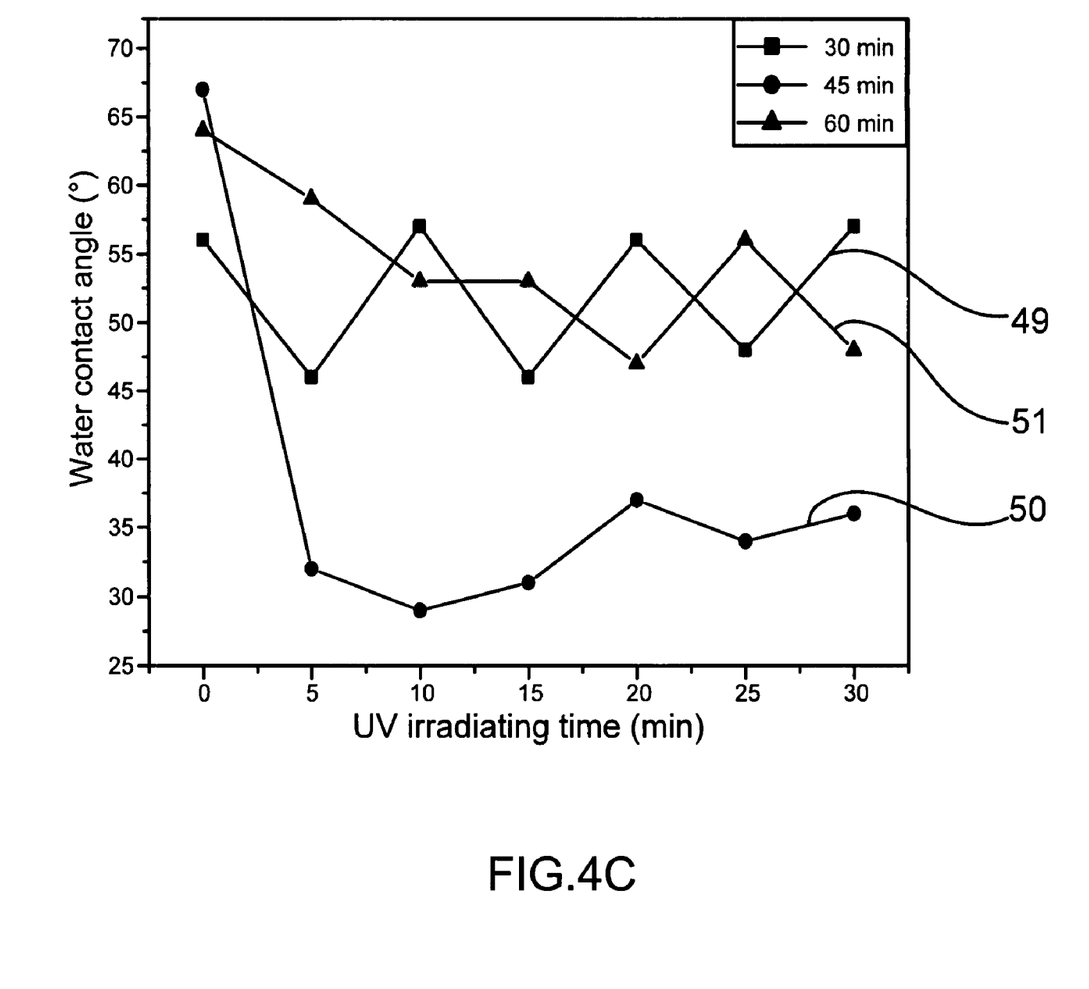

Please refer to FIG. 4B and FIG. 4C, which are a first and a second views showing the water contact angle. As shown in the figures, the plasma activation treatment in step (b) is processed for 30 seconds (sec), 3 min, 5 min 10 min, 15 min, 30 min, 45 min or 60 min. In addition to the plasma activation treatment together with being irradiated with a UV light for 5 min to 30 min, a various water contact angle is obtained for the various $TiO_x$ film onto stretchable Teflon with a various time for plasma activation treatment and a various time for UV irradiation.

In FIG. 4B, a first curve 44, a second curve 45, a third curve 46, a fourth curve 47 and a fifth curve 48 are shown. The first curve 44 shows a change in water contact angle after 30 sec of plasma activation treatment together with 5 to 30 min of UV light irradiation; the second curve 45, 3 min of plasma activation treatment together with 5 to 30 min of UV light irradiation; the third curve 46, 5 min of plasma activation treatment together with 5 to 30 min of UV light irradiation; the fourth curve 47, 10 min of plasma activation treatment together with 5 to 30 min of UV light irradiation; and the fifth curve 48, 15 min of plasma activation treatment together with 5 to 30 min of UV light irradiation.

In FIG. 4C, a sixth curve 49, a seventh curve 50 and a eighth curve 51 are shown. The sixth curve 49 shows a change in water contact angle after 30 min of plasma activation treatment and 5 min to 30 min of UV light irradiation; the seventh curve 50, 45 min of plasma activation treatment together with 5 to 30 min of UV light irradiation; and the eighth curve 51, 60 min of plasma activation treatment together with 5 to 30 min of UV light irradiation.

From the above two figures, it is found that, before processing the plasma activation treatment, the stretchable Teflon with the organic Ti solution has a water contact angle as high as 80 to 85 degrees (°). After processing the plasma activation treatment for a various time, the plasma is reacted with the organic Ti solution on the surface of the stretchable Teflon, which breaks a structure of a TIP precursor in the organic Ti solution so that Ti containing peroxide is obtained on the surface of the stretchable Teflon. During the UV light irradiation, pairs of electron and hole are increased and activated so that oxidation and reduction to $O_2$ and water molecules are accelerated to obtain hydrophile on the surface. Take the seventh curve 50, for example. After processing the UV light irradiation for 5 min and the plasma activation treatment for 45 min, the water contact angle of the $TiO_x$ film onto stretchable Teflon is reduced from 67° to 32°. Take the eighth curve 51 as another example. The plasma activation treatment is prolonged to 60 min; and the water contact angle of the $TiO_x$ film onto stretchable Teflon is increased from 56° to 59°. Yet, according to the fourth curve 47, when the plasma activation treatment is shortened to 10 min, the water contact angle of the $TiO_x$ film onto stretchable Teflon is reduced from 77° to 46°. Therefore, the longer the plasma activation treatment is processed, the better the Ti—O structure is formed on the surface of the stretch able Teflon through the reaction with the organic Ti solution.

Figure 4D:
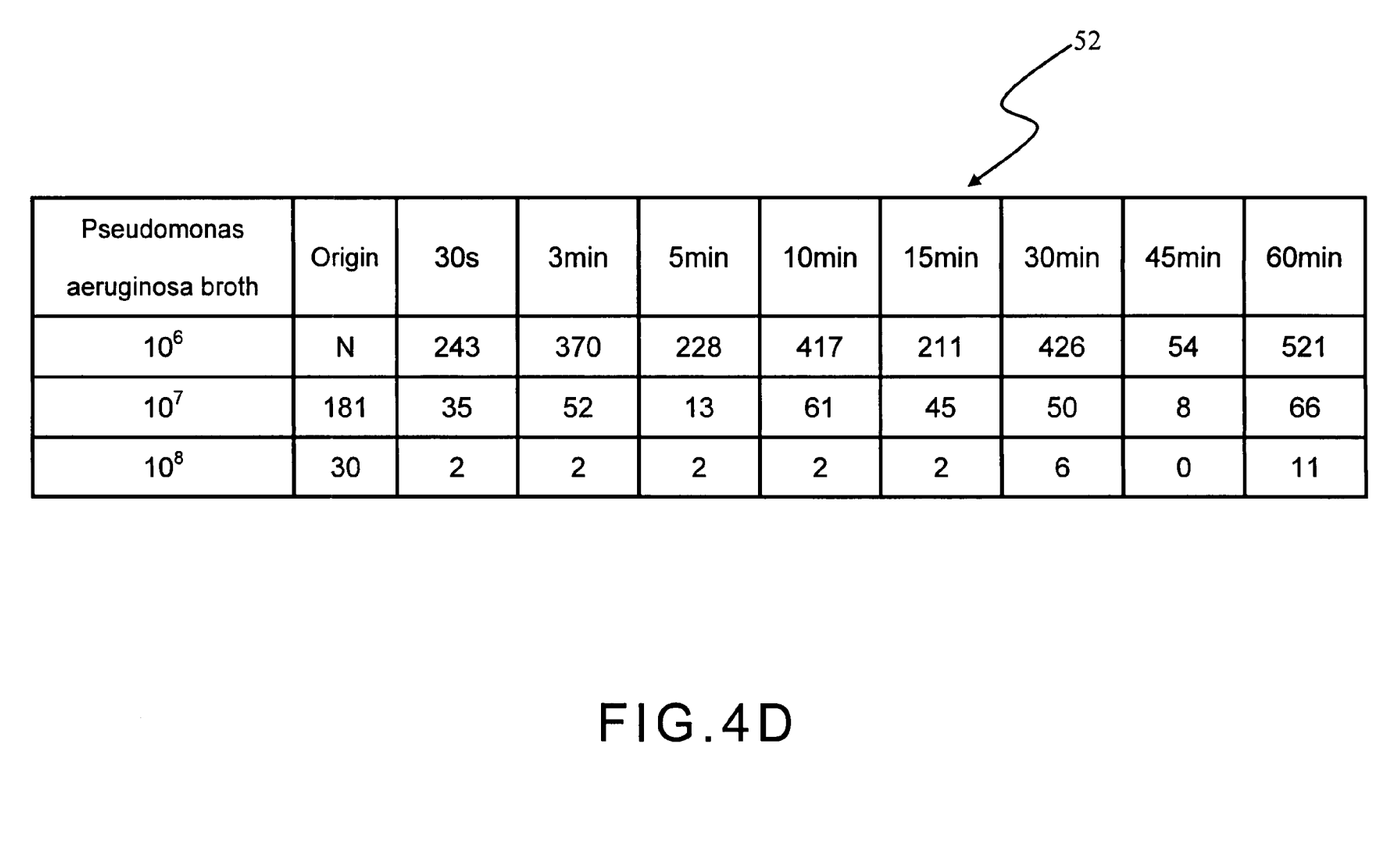
FIG. 4D is the view showing the anti-bacterial effect.

Please refer to FIG. 4D, which is a view showing an anti-bacterial effect. As shown in the figure, the $TiO_x$ film on stretchable Teflon obtained in the third preferred embodiment is processed through an anti-bacterial test by using pseudomonas aeruginosa. And a best time duration for plasma activation treatment 52 is obtained at 45 min for a best anti-bacterial effect.

To sum up, the present invention is a plasma method for a $TiO_x$ biomedical material onto polymer sheet, where, through a simple procedure, a biomedical material having anti-bacterial effect, hydrophile and good bio-compatibility is obtained.

The preferred embodiments herein disclosed are not intended to unnecessarily limit the scope of the invention. Therefore, simple modifications or variations belonging to the equivalent of the scope of the claims and the instructions disclosed herein for a patent are all within the scope of the present invention.

What is claimed is:

1. A plasma method for depositing a titanium oxide ($TiO_x$) biomedical material onto a hydrophilic polymer film, comprising steps of:
   (a) obtaining said hydrophilic polymer film coated with an organic titanium (Ti) solution formed through a sol-gel method, said sol-gel method comprising steps of:
   (a1) dissolving a precursor of Ti Isopropoxide (TIP) into an organic solution;
   (a2) obtaining an organic Ti solution from said organic solution by using ultrasonic waves; and
   (a3) spin-coating a layer of said organic Ti solution on a surface of said hydrophilic polymer film; and
   (b) processing a plasma activation treatment to said hydrophilic polymer film coated with said organic Ti solution under a vacuum pressure with oxygen ($O_2$) having a pressure to obtain a TiOx film onto said hydrophilic polymer film.

2. The method according to claim 1, wherein said hydrophilic polymer film in step (a) is made of a material selected from the group consisting of hexamethyldisilazane (HMDSZ), itaconic acid and acryl amide.

3. The method according to claim 1, wherein said vacuum pressure in step (b) is a pressure below 50 mtorr.

4. The method according to claim 1, wherein said $O_2$ in step (b) has a pressure between 150 mtorr and 250 mtorr.

5. The method according to claim 1, wherein said plasma activation treatment in step (b) is processed for more than 10 minutes (min) under a working power greater than 50 watts (W).

6. The method according to claim 1, wherein said hydrophilic polymer film in step (b) is made of a material selected from the group consisting of a stretchable Teflon and a polylactic-co-glycolic acid (PLGA).

7. A plasma method for depositing a $TiO_x$ biomedical material onto a hydrophilic polymer film, comprising steps of:
(a) obtaining said hydrophilic polymer film and coating said hydrophilic polymer film with an organic Ti solution formed through a sol-gel method;
(b) processing a plasma activation treatment to said hydrophilic polymer film coated with said organic Ti solution under a vacuum pressure below 50 mtorr with $O_2$ having a pressure between 150 mtorr and 250 mtorr to obtain a $TiO_x$ film said hydrophilic polymer film; and
(c) process a copolymerization in a surface grafting to said $TiO_x$ film onto said hydrophilic polymer film.

8. The method according to claim 7, wherein said hydrophilic polymer film in step (c) is made of a material having a hydrophilic HMDSZ; and
wherein said material is selected from the group consisting of a stretchable Teflon and a PLGA.

9. The method according to claim 7, wherein said sol-gel method in step (a) comprises steps of:
(a1) dissolving a precursor of TIP into an organic solution;
(a2) obtaining an organic Ti solution from said organic solution by using ultrasonic waves; and
(a3) spin-coating a layer of said organic Ti solution on a surface of said polymer film having hydrophilic HMDSZ.

10. The method according to claim 7, wherein said plasma activation treatment in step (b) is processed under a working power between 10 W and 100 W.

11. The method according to claim 7, wherein said plasma activation treatment in step (b) is processed for a period between 5 min and 100 min.

12. The method according to claim 7, wherein said copolymerization in said surface grafting in step (c) comprises steps of:
(c1) depositing said $TiO_x$ film onto said hydrophilic polymer film in a solution of N-Vinyl-2-pyrrolidinone (NVP) and adding an amount of a vitamin $B_2$ solution to said NVP solution and processing nitrogen for a period of time;
(c2) irradiating said NVP solution having said $TiO_x$ film onto said hydrophilic polymer film with an ultra-violet (UV) light; and
(c3) moving out said $TiO_x$ film onto said hydrophilic polymer film to be washed with a distilled water to remove homopolymer and unreacted monomer.

13. The method according to claim 12, wherein a mixture rate of said NVP solution and said vitamin $B_2$ solution in step (c1) is 10:1.

14. The method according to claim 12, wherein said nitrogen in step (c1) is processed shorter than 30 min.

15. The method according to claim 12, wherein said UV light in step (c2) is irradiated for a period between 5 min and 30 min.

16. The method according to claim 12, wherein said washing in step (c3) is shorter than 40 hours.

17. The method according to claim 7, wherein said NVP solution in step (c1) has an amount less than 30 weight percents (wt %).

\* \* \* \* \*